United States Patent
Hori et al.

(10) Patent No.: US 7,833,406 B2
(45) Date of Patent: Nov. 16, 2010

(54) GENE DETECTION METHOD, AND INTERCALATOR

(75) Inventors: Junichi Hori, Ehime (JP); Ryusuke Murayama, Ehime (JP); Jinpei Tabata, Ehime (JP); Katsuhiko Bando, Ehime (JP); Naoyoshi Egashira, Hiroshima (JP)

(73) Assignee: Panasonic Corporation, Osaka (JP)

( * ) Notice: Subject to any disclaimer, the term of this patent is extended or adjusted under 35 U.S.C. 154(b) by 828 days.

(21) Appl. No.: 11/631,609

(22) PCT Filed: Jun. 30, 2005

(86) PCT No.: PCT/JP2005/012080

§ 371 (c)(1),
(2), (4) Date: Jan. 5, 2007

(87) PCT Pub. No.: WO2006/003991

PCT Pub. Date: Jan. 12, 2006

(65) Prior Publication Data

US 2009/0000962 A1    Jan. 1, 2009

(30) Foreign Application Priority Data

Jul. 6, 2004    (JP) .............................. 2004-199157

(51) Int. Cl.
G01N 27/327    (2006.01)
G01N 21/76    (2006.01)
C09K 3/00    (2006.01)

(52) U.S. Cl. .............................. 205/777.5; 204/403.01; 422/52; 436/172; 252/700

(58) Field of Classification Search .............. 205/777.5, 205/779, 780.5, 792; 204/403.01, 775; 422/52; 436/172; 252/700
See application file for complete search history.

(56) References Cited

U.S. PATENT DOCUMENTS 5,503,721 A * 4/1996 Hearst et al. ............. 204/157.6

(Continued)

FOREIGN PATENT DOCUMENTS

JP    2573443    10/1996

(Continued)

OTHER PUBLICATIONS

Leng et al. Base Specific and Regioselective Chemical Cross-linking of Daunorubicin to DNA, J. Amer. Chem. Soc. vol. 118, No. 20, May 22, 1996, pp. 4731-4738.*

(Continued)

*Primary Examiner*—Alex Noguerola
(74) *Attorney, Agent, or Firm*—Wenderoth, Lind & Ponack, LLP (57) ABSTRACT

A gene detection method for detecting a gene having a specific sequence with high sensitivity is provided. The gene detection method comprises a double-stranded nucleic acid formation step of forming double-stranded nucleic acid by hybridizing a nucleic acid probe immobilized on an electrode and a gene sample; a step of adding an intercalator which comprises a compound having a double-stranded nucleic acid binding site Ia that is specifically intercalated into the double-stranded nucleic acid and is covalently bonded to the double-stranded nucleic acid by light irradiation, an electrochemical active site Fa having electrochemical activity, and a connecting site La for connecting the double-stranded nucleic acid binding site Ia and the electrochemical active site Fa, and has an substitution group comprising one of compounds represented by -Lb-Ib and -Lc-Fb or a combination of the both compounds, at each of the respective sites; a light irradiation step of covalently bonding the double-stranded nucleic acid and the intercalator; and a detection step of detecting the intercalator covalently bonded to the double-stranded nucleic acid by electrochemical measurement.

23 Claims, 1 Drawing Sheet

X : electrode on which double-stranded nucleic acid is formed
Y : electrode on which no double-stranded nucleic acid is formed

U.S. PATENT DOCUMENTS

| | | |
|---|---|---|
| 5,776,672 A | 7/1998 | Hashimoto et al. |
| 6,461,820 B1 * | 10/2002 | Barton et al. ............. 435/6 |
| 2003/0124572 A1 * | 7/2003 | Umek et al. ............. 435/6 |
| 2005/0032049 A1 * | 2/2005 | Azek et al. ............. 435/6 |

FOREIGN PATENT DOCUMENTS

| | | |
|---|---|---|
| JP | 3233851 | 9/2001 |
| JP | 2002-531829 | 9/2002 |
| JP | 2003-322653 | 11/2003 |
| JP | 2003-294700 | 10/2005 |
| WO | 00/33078 | 6/2000 |

OTHER PUBLICATIONS

Copeland et al. ("DNA Cross-linking with Metallointercalator-Peptide Conjugates," Biochemistry 2002, 41, 12785-12797).*

* cited by examiner

Fig.1

X : electrode on which double-stranded nucleic acid is formed

Y : electrode on which no double-stranded nucleic acid is formed

US 7,833,406 B2

GENE DETECTION METHOD, AND INTERCALATOR

This application is a 371 of PCT/JP2005/012080, filed Jun. 30, 2005, which claims priority from Japanese application JP 2004-199157, filed Jul. 6, 2004.

TECHNICAL FIELD

The present invention relates to a gene detection method for detecting a specific gene sequence that exists in a sample with high sensitivity, and more particularly, to a technique for electrochemically detecting a gene by an intercalator.

BACKGROUND ART

In a conventional DNA chip for electrochemically detecting a specific gene sequence, a single-stranded nucleic acid probe having a base sequence that is complementary to a target gene to be detected is immobilized on an electrode surface, and the nucleic acid probe and the target gene sample that is denatured to a single strand are hybridized, and thereafter, an intercalator which is electrochemically active and specifically binds to the double-stranded nucleic acid comprising the nucleic acid probe and the target gene sample is added to a reaction system for the nucleic acid probe and the gene sample, and then the intercalator bonded to the double-stranded nucleic acid is detected by performing electrochemical measurement through the electrode, whereby the nucleic acid probe that is hybridized with the target gene sample is detected to confirm existence of the target gene (for example, refer to Patent Document 1 (U.S. Pat. No. 2,573,443) and Patent Document 2 (U.S. Pat. No. 3,233,851)).

The intercalator indicates a substance that recognizes the double-stranded nucleic acid and specifically binds to the double-stranded nucleic acid. The intercalator has a tabular intercalation base such as phenyl in a molecule, and binds to the double-stranded nucleic acid by that the intercalation base is intercalated between a base pair and a base pair of the double-stranded nucleic acid. This binding of the intercalator and the double-stranded nucleic acid is a binding due to electrostatic interaction or hydrophobic interaction, and it is a binding caused by equilibrium reaction in which intercalation of the intercalator between the base pairs of the double-stranded nucleic acid and separation of the intercalator from between the base pairs are repeated at a constant speed.

Among the above-mentioned intercalators, there is a substance that causes electrically reversible oxidation-reduction reaction. By using such intercalator that causes electrochemically reversible oxidation-reduction reaction, it is possible to detect existence of the intercalator bonded to the double-stranded nucleic acid by measuring the electrochemical change. As an output signal of this electrochemical change, there is current or luminescence that occurs during the oxidation-reduction.

That is, in the conventional gene detection method, it is important that the intercalator is specifically bonded to only the double-stranded nucleic acid, and that the amount of the intercalator bonded to the double-stranded nucleic acid is accurately detected.

However, the intercalator used for the conventional gene detection is nonspecifically adsorbed to the single-stranded nucleic acid probe and to the electrode surface on which the nucleic acid probe is immobilized, due to chemical bonding such as coordinate bonding or covalent bonding, or electrostatic interaction or hydrophobic interaction. The nonspecifically adsorbed intercalator causes background noise when detecting the amount of the intercalator bonded to the double-stranded nucleic acid, leading to reduction in the detection sensitivity.

In order to solve this problem, in the above-mentioned detection method, it is necessary to perform a washing process for removing the intercalator that is nonspecifically adsorbed to the single-stranded nucleic acid probe and the electrode surface, after addition of the intercalator.

DISCLOSURE OF THE INVENTION

Problems to be Solved by the Invention

However, as described above, since the intercalator and the double-stranded nucleic-acid are bonded to each other by electrostatic interaction or hydrophobic interaction, the bonding force is weak, and therefore, the intercalator bonded to the double-stranded nucleic acid is undesirably dissociated during the washing process for removing the intercalator that is nonspecifically adsorbed to the single-stranded nucleic acid probe and to the electrode surface on which the nucleic acid probe is immobilized, whereby the detection sensitivity is reduced conversely.

On the other hand, when it is considered to prevent the dissociation of the intercalator bonded to the double-stranded nucleic acid during the washing process, the intercalator that is nonspecifically adsorbed to the single-stranded nucleic acid probe and the electrode surface, which causes background noise, cannot be sufficiently removed, leading to reduction in the detection sensitivity.

Furthermore, since the bonding reaction between the intercalator and the double-stranded nucleic acid is equilibrium reaction, the rate at which the intercalator is intercalated between the base pairs of the double-stranded nucleic acid is low, resulting in low detection sensitivity.

The present invention is made to solve the above-mentioned problems and has for its object to provide a gene detection method and an intercalator, which can detect a target gene in a specimen with high sensitivity.

Measures to Solve the Problems

In order to solve the above-mentioned problems, according to the present invention, a gene detection method for detecting a gene having a specific sequence comprises a gene sample conformation step of conforming a gene sample by denaturing a gene to be detected into a single strand; an immobilization step of immobilizing, onto an electrode, a single-stranded nucleic acid probe having a base sequence that is complementary to a base sequence of the gene sample to be detected; a double-stranded nucleic acid formation step of adding the gene sample to the electrode on which the nucleic acid probe is immobilized, thereby forming a double-stranded nucleic acid in which the nucleic acid probe and the gene sample are hybridized; an intercalator addition step of adding, to the electrode on which the double-stranded nucleic acid is formed, an intercalator that has a substitution group comprising one of compounds represented by -Lb-Ib and -Lc-Fb or a combination of the both compounds, at the respective sites shown in a general formula (1) as follows:

$$\text{Fa-La-Ia} \tag{1}$$

[wherein Fa and Fb are electrochemical active sites having electrochemical activity, Ia and Ib are double-stranded nucleic acid binding sites which are specifically intercalated into the double-stranded nucleic acid, and are covalently bonded to the double-stranded nucleic acid by light irradiation, and La, Lb, and Lc are connecting sites which connect the double-stranded nucleic acid binding sites with the electrochemical active sites]; a light irradiation step of covalently bonding the double-stranded nucleic acid and the intercalator by performing light irradiation; and a detection step of detecting the intercalator that is covalently bonded to the double-stranded nucleic acid, by electrochemical measurement.

Therefore, the double-stranded nucleic acid in which the gene sample and the nucleic acid probe are hybridized, and the intercalator can be bonded irreversibly and firmly. As a result, when the gene sample is washed to remove the intercalator that is nonspecifically adhered to the single-stranded nucleic acid probe and the electrode surface, the intercalator bonded to the double-stranded nucleic acid is prevented from dissociating, whereby the target gene sample can be detected with high sensitivity. Further, the number of the double-stranded nucleic acid binding sites and the number of the electrochemical active sites are increased, and consequently, the rate of intercalation into the base pairs of the double-stranded nucleic acid is increased, whereby the electrochemical output signal from the intercalator bonded to the double-stranded nucleic acid is also increased, resulting in highly sensitive detection of the gene sample.

Further, in the gene detection method of the present invention, the Fa and the Fb comprise the same compound, and the Ia and the Ib comprise the same compound.

Therefore, quantitative detection of the target gene can be carried out.

Further, in the gene detection method of the present invention, the detection step applies voltage to the electrode, and measures an amount of electrochemiluminescence that is caused by the intercalator covalently bonded to the double-stranded nucleic acid.

Therefore, when voltage is applied to the electrode, more favorable electrochemiluminescence amount can be obtained, whereby the gene sample can be detected with higher sensitivity.

Further, in the gene detection method of the present invention, the Ia and the Ib comprise a compound having photosensitivity.

Therefore, the intercalator intercalated into the double-stranded nucleic acid is firmly and irreversibly bonded to the double-stranded nucleic acid, whereby the intercalator is prevented from dissociating from the double-stranded nucleic acid even when strong washing is carried out, and consequently, the gene sample can be detected with high sensitivity.

Further, in the gene detection method of the present invention, the compound having photosensitivity is furocoumarin derivative.

Further, in the gene detection method of the present invention, the furocoumarin derivative is psoralen derivative.

Further, in the gene detection method of the present invention, the Fa and the Fb comprise a compound having oxidation-reduction property.

Therefore, the existence of the gene as a detection target can be detected by measuring an oxidation-reduction current that occurs during oxidation-reduction reaction.

Further, in the gene detection method of the present invention, the compound having oxidation-reduction property is a compound indicating electrochemiluminescence.

Therefore, when voltage is applied to the electrode, the intercalator bonded to the double-stranded nucleic acid that is immobilized onto the electrode occurs oxidation-reduction reaction and produces luminescence, and the gene as a detection target can be detected by measuring the amount of electrochemiluminescence.

Further, in the gene detection method of the present invention, the compound indicating electrochemiluminescence is one selected from a group consisting of a metal complex having a heterocyclic system compound as a ligand, rubrene, anthracene, coronene, pyrene, fluoranthene, chrysene, phenanthrene, perylene, binaphthyl, and octatetraene.

Further, in the gene detection method of the present invention, the metal complex having a heterocyclic system compound as a ligand is a metal complex having a pyridine site as a ligand.

Further, in the gene detection method of the present invention, the metal complex having a pyridine site as a ligand is one of a metal bipyridine complex and a metal phenanthroline complex.

Further, in the gene detection method of the present invention, a center metal of the metal complex having a heterocyclic system compound as a ligand is one of ruthenium and osnium.

Further, an intercalator of the present invention is represented by a general formula (1) as follows:

$$Fa\text{-}La\text{-}Ia \qquad (1)$$

[wherein Fa is an electrochemical active site having electrochemical activity, Ia is a double-stranded nucleic acid binding site which is specifically intercalated into the double-stranded nucleic acid and is covalently bonded to the double-stranded nucleic acid by light irradiation, and La is a connecting site which connects the double-stranded nucleic acid binding site with the electrochemical active site]; and this intercalator has a substitution group comprising one of or a combination of both of compounds represented by -Lb-Ib and -Lc-Fb [wherein Ib is a double-stranded nucleic acid binding site which is specifically intercalated into the double-stranded nucleic acid and is covalently bonded to the double-stranded nucleic acid by light irradiation, Fb is an electrochemical active site having electrochemical activity, and Lb and Lc are connecting sites], at the respective sites shown in the general formula (1).

Therefore, it is possible to provide an intercalator which can increase the rate of intercalation of the intercalator into the double-stranded nucleic acid to detect the target gene sample with high sensitivity.

Further, in the intercalator of the present invention, the Fa and the Fb comprise the same compound, and the Ia and the Ib comprise the same compound.

Therefore, quantitative detection of the target gene can be carried out.

Further, in the intercalator of the present invention, the Ia and the Ib comprise a compound having photosensitivity.

Further, in the intercalator of the present invention, the compound having photosensitivity is furocoumarin derivative.

Therefore, the intercalator intercalated into the double-stranded nucleic acid is firmly and irreversibly bonded to the double-stranded nucleic acid, whereby the intercalator is prevented from dissociating from the double-stranded nucleic acid even when strong washing is carried out, and consequently, the gene sample can be detected with high sensitivity.

Further, in the intercalator of the present invention, the furocoumarin derivative is psoralen derivative.

Further, in the intercalator of the present invention, the Fa and the Fb comprise a compound having oxidation-reduction property.

Therefore, the existence of the gene as a detection target can be detected by measuring an oxidation-reduction current that occurs during oxidation-reduction reaction.

Further, in the intercalator of the present invention, the compound having oxidation-reduction property is a compound indicating electrochemiluminescence.

Therefore, the existence of the gene as a detection target can be detected by measuring the electrochemiluminescence.

Further, in the intercalator of the present invention, the compound indicating electrochemiluminescence is one selected from a group consisting of a metal complex having a heterocyclic system compound as a ligand, rubrene, anthracene, coronene, pyrene, fluoranthene, chrysene, phenanthrene, perylene, binaphthyl, and octatetraene.

Further, in the intercalator of the present invention, the metal complex having a heterocyclic system compound as a ligand is a metal complex having a pyridine site as a ligand.

Further, in the intercalator of the present invention, the metal complex having a pyridine site as a ligand is one of a metal bipyridine complex and a metal phenanthroline complex.

Further, in the intercalator of the present invention, a center metal of the metal complex having a heterocyclic system compound as a ligand is one of ruthenium and osnium.

EFFECTS OF THE INVENTION

According to the gene detection method of the present invention, when detecting a gene having a specific sequence, an intercalator that is electrochemically active and covalently bonded to the double-stranded nucleic acid by light irradiation is used. Therefore, the double-stranded nucleic acid and the intercalator can be covalently bonded by light irradiation, whereby the double-stranded nucleic acid and the intercalator can be bonded irreversibly and firmly. As a result, when the sample is washed to remove the intercalator that is nonspecifically adsorbed to the single-stranded nucleic acid and the electrode surface, the intercalator bonded to the double-stranded nucleic acid is prevented from dissociating, whereby the target gene sample can be detected with high sensitivity.

Further, according to the gene detection method of the present invention, since the intercalator has plural electrochemical active sites or plural double-stranded nucleic acid bonding sites, the rate of intercalation into the base pairs of the double-stranded nucleic acid is increased, and further, the electrochemical output signal from the intercalator bonded to the double-stranded nucleic acid is also increased, whereby the gene sample as a detection target can be detected with higher sensitivity.

Further, since the intercalator of the present invention includes the double-stranded nucleic acid binding site that is covalently bonded to the double-stranded nucleic acid by light irradiation, the intercalator and the double-stranded nucleic acid can be firmly and irreversibly bonded, thereby providing the intercalator that does not dissociate from the double-stranded nucleic acid even in the washing process.

Furthermore, since the intercalator of the present invention includes plural electrochemical active sites or plural double-stranded nucleic acid binding sites, the rate of intercalation of the intercalator into the base pairs of the double-stranded nucleic acid can be increased, and further, the electrochemical output signal from the intercalator bonded to the double-stranded nucleic acid can be increased.

BEST MODE TO EXECUTE THE INVENTION

Hereinafter, a gene detection method according to the present invention will be described in detail. In the following embodiments of the invention, a gene sample is obtained by liberating a double-stranded nucleic acid from an arbitrary sample including, for example, blood, white blood cell, blood serum, urine, feces, semen, saliva, cultured cell, tissue cell such as cells of various organs, and other genes, by disrupting the cells in the sample, and then dissociating the double-stranded nucleic acid into a single-stranded nucleic acid by thermal treatment or alkali treatment. Further, the gene sample according to the embodiments of the present invention may be a nucleic acid segment that is cut off by a restriction enzyme and purified by such as separation due to electrophoresis.

Embodiment 1

Hereinafter, a gene detection method according to a first embodiment and an intercalator used for the first embodiment will be described.

Initially, a gene sample to be a test target is formed. This gene sample is formed as described above, that is, a cell in an arbitrary sample is disrupted to liberate a double-stranded nucleic acid and then the double-stranded nucleic acid is denatured into a single-stranded nucleic acid by thermal treatment or alkali treatment.

At this time, the cell in the sample can be disrupted by an ordinary method, such as externally applying a physical effect like vibration or ultrasonic wave. Further, it is also possible to liberate the nucleic acid from the cell by using a nucleic acid extraction solution (for example, a surface-active agent such as SDS, Triton-X, or Tween-20, or a solution including such as saponin, EDTA, or protease).

Next, a single-stranded nucleic acid probe having a base sequence that is complementary to the gene sequence to be detected is formed.

As for this nucleic acid probe, it is possible to use a nucleic acid that is obtained by cutting off a nucleic acid extracted from a biologic sample, with a restriction enzyme, and purifying the nucleic acid by electrophoresis separation or the like, or a single-stranded nucleic acid obtained by chemical synthesis. In the case of using the nucleic acid extracted from the biologic sample, it is preferable to dissociate the same into a single-stranded nucleic acid by thermal treatment or alkali treatment.

Thereafter, the nucleic acid probe obtained as described above is immobilized onto an electrode.

Any electrode may be used in the present invention so long as it can be used as an electrode. For example, there may be used a noble metal electrode such as gold, platinum, platinum black, palladium, or rhodium, a carbon electrode such as graphite, glassy carbon, pyrolytic graphite, carbon paste, or carbon fiber, an oxide electrode such as titanic-oxide, tin oxide, manganese oxide, or lead oxide, and a semiconductor electrode such as Si, Ge, ZnO, CdS, TiO, or GaAs. These electrodes may be covered with a conductive polymer, thereby to prepare a more stable probe immobilized electrode.

As a method for immobilizing the nucleic acid probe to the electrode, a well-know method is adopted. For example, when the electrode comprises gold, thiol group is introduced to a 5'- or 3'-terminal (preferably, 5'-terminal) of the nucleic acid probe to be immobilized, and the nucleic acid probe is immobilized to the gold electrode via covalent bond between gold and sulfur. A method for introducing the thiol group to the nucleic acid probe is described in "M. Maeda et al., Chem. Lett., 1805~1808 (1994)", and "B. A. Connolly, Nucleic Acids Res., 13, 4484 (1985)".

That is, the nucleic acid probe having the thiol group obtained by the above-mentioned method is dropped onto the gold electrode, and the gold electrode is left for a few hours under a low temperature, whereby the nucleic acid probe is immobilized onto the electrode, resulting in a nucleic acid probe.

Another method is as follows. For example, when the electrode comprises glassy carbon, initially, the glassy carbon is oxidized with potassium permanganate to introduce carboxylic acid group onto the electrode surface, whereby the nucleic acid probe is immobilized onto the surface of the glassy carbon electrode by amide binding. An actual method for immobilizing the nucleic acid probe onto the glassy carbon electrode is described in "K. M. Millan et al., Analytical Chemistry, 65, 2317~2323 (1993)".

Next, the electrode onto which the nucleic acid probe is immobilized is brought into contact with a solution including the gene sample. Thereby, the nucleic acid probe and the gene sample having a base sequence that is complementary to the base sequence of the nucleic acid probe are hybridized, thereby generating a double-stranded nucleic acid. Since the method for hybridizing the nucleic acid probe and the gene sample is well known, a description thereof will be omitted.

After the double-stranded nucleic acid is thus formed on the electrode, an intercalator is added to the electrode on which the double-stranded nucleic acid is formed so that the intercalator is intercalated into and reacted with the double-stranded nucleic acid. The intercalator may be added into the sample before the formation of the double-stranded nucleic acid, that is, before the hybridization reaction.

Thereafter, the double-stranded nucleic acid to which the intercalator is added is irradiated with light to make covalent bonding between the double-stranded nucleic acid and the intercalator.

Hereinafter, a description will be given of the intercalator to be intercalated into the double-stranded nucleic acid.

A substance that is specifically intercalated into the double-stranded nucleic acid and covalently bonded to the double-stranded nucleic acid by light irradiation is adopted as the intercalator of the present invention. Therefore, since the intercalator is firmly and irreversibly bonded to the double-stranded nucleic acid, the intercalator bonded to the double-stranded nucleic acid is not dissociated from the double-stranded nucleic acid during the following washing process, and the unreacted intercalator that is not bonded to the double-stranded nucleic acid can be removed during the washing process.

Further, a substance that is electrochemically active is adopted as the intercalator of the present invention. Therefore, it is possible to detect existence of the double-stranded nucleic acid, i.e., the gene sample, with high sensitivity, by detecting an electrochemical signal which is derived from the intercalator specifically bonded to the double-stranded nucleic acid.

An intercalator that satisfies the above-mentioned two characteristics is a compound having a double-stranded nucleic acid binding site Ia that is specifically intercalated into the double-stranded nucleic acid and covalently bonded to the double-stranded nucleic acid by light irradiation, an electrochemical active site Fa that has electrochemical activity, and a connecting site La that connects the double-stranded nucleic acid binding site Ia with the electrochemical active site Fa.

For example, such intercalator can be expressed by the following general formula (1).

$$\text{Fa-La-Ia} \qquad (1)$$

(in the formula, Fa denotes the electrochemical active site that is electrochemically active, Ia denotes the double-stranded nucleic acid binding site having a site that is linked with the double-stranded nucleic acid by light irradiation, and La denotes the connecting site that connects the Ia and the Fa).

As a substance that can be used as the double-stranded nucleic acid intercalation group Ia shown in the general formula (1), there is a photosensitive compound that is specifically intercalated into the double-stranded nucleic acid and covalently bonded to the double-stranded nucleic acid by light irradiation.

As the photosensitive compound, for example, furocoumarin derivative is adopted, and particularly, psoralen derivative is preferable. When the psoralen derivative is intercalated into the double-stranded nucleic acid, it causes noncovalent interaction with the double-stranded nucleic acid. Further, when it is irradiated with a long wavelength ultraviolet ray (300~400 nm), the psoralen derivative portion intercalated into the double-stranded nucleic acid forms stable covalent bonding, and consequently, the intercalator and the double-stranded nucleic acid can be firmly and irreversibly bonded.

Accordingly, when washing the intercalator that is nonspecifically adsorbed to the single-stranded nucleic acid probe and the electrode surface in the following washing process, the intercalator bonded to the double-stranded nucleic acid is prevented from dissociating, and therefore, only the intercalator that is nonspecifically adsorbed to the single-stranded nucleic acid probe and the electrode surface can be reliably removed by performing strong washing in the washing process.

As specific examples of the psoralen derivative, there are psoralen, methoxypsoralen, and trimethylpsoralen.

As a substance that can be used as the electrochemical active site Fa shown in the general formula (1), any substance may be used without restriction so long as it is electrochemically detectable. For example, there may be used a compound having oxidation-reduction property, which is detectable by measuring oxidation-reduction current that occurs during reversible oxidation-reduction reaction. By measuring the oxidation-reduction current that occurs during reversible oxidation-reduction reaction, the existence of the double-stranded nucleic acid, i.e., the target gene, can be detected.

As examples of the compound having oxidation-reduction property, there are ferrocene, catecholamine, a metal complex having a heterocyclic system compound as a ligand, rubrene, anthracene, coronene, pyrene, fluoranthene, chrysene, phenanthrene, perylene, binaphthyl, octatetraene, and viologen.

Further, among the above-mentioned metal complex having a heterocyclic system compound as a ligand, rubrene, anthracene, coronene, pyrene, fluoranthene, chrysene, phenanthrene, perylene, binaphthyl, and octatetraene, some of them occur electrochemiluminescence during oxidation-reduction reaction, and when such substance that occurs electrochemiluminescence is used as the intercalator, the existence of the gene sample can also be detected by measuring the luminescence.

Further, as examples of the metal complex having a heterocyclic system compound as a ligand, there are heterocyclic system compounds including oxygen or nitrogen, for example, metal complexes having a pyridine site or a pyran site as ligands, and particularly, a metal complex having a pyridine site as a ligand is preferable. As examples of the metal complex having a pyridine site as a ligand, there are a metal bipyridine complex and a metal phenanthroline complex.

Further, as examples of a center metal of the metal complex having a heterocyclic system compound as a ligand, there are ruthenium, osnium, zinc, cobalt, platinum, chrome, molybdenum, tungsten, technetium, rhenium, rhodium, iridium, palladium, copper, indium, lanthanum, praseodymium, neodymium, and samarium. Particularly, a complex having ruthenium or osnium as a center metal has favorable electrochemiluminescent characteristic. As examples of a material having favorable electrochemiluminescent characteristic, there are ruthenium bipyridine complex, ruthenium phenanthroline complex, osnium bipyridine complex, and osnium phenanthroline complex.

In the general formula (1), as for a substance that can be used as the connecting site La, the linker sequence of the connecting site is not particularly restricted so long as it can connect the electrochemical active site Fa and the double-stranded nucleic acid binding site Ia. For example, alkyl group, —O— group, —CO— group, —NH— group, or a group comprising a combination of these groups can be used.

In the intercalator of the present invention, each of the electrochemical active site Fa, the connecting site La, and the double-stranded nucleic acid binding site Ia has a substitution group comprising one of compounds represented by -Lb-Ib and -Lc-Fb or a combination of the both compounds, in the general formula (1). However, the Ib is a double-stranded nucleic acid binding site that is specifically intercalated into the double-stranded nucleic acid and is covalently bonded with the double-stranded nucleic acid by light irradiation, the Fb is an electrochemical active site having electrochemical property, and the Lb and Lc are connecting sites that connect the double-stranded nucleic acid binding site and the electrochemical active site.

The introduction position of the substitution group represented by -Lb-Ib and -Lc-Fb into the general formula (1) is not particularly restricted, and the substitution group may be introduced in any of the sites Fa, La, and Ia. Further, the introduction number of the substitution group into the general formula (1) is not particularly restricted.

The substitution group may be constituted by -Lb-Ib or -Lc-Fb alone, or it may be constituted by a combination of -Lb-Ib and -Lc-Fb. For example, the substitution group may have a serial construction in which a plurality of -Lb-Ib alone or -Lc-Fb alone are connected in series, or a serial construction in which a plurality of -Lb-Ib and -Lc-Fb are complexly connected in series, or a branch construction in which a plurality of -Lb-Ib or -Lc-Fb are complexly bonded to each of Lb and lc of -Lb-Ib and -Lc-Fb, respectively, or a complex construction comprising the serial construction and the branch construction.

A substance to be used as the double-stranded nucleic acid binding site Ib is a substance that is specifically intercalated into the double-stranded nucleic acid and is covalently bonded to the double-stranded nucleic acid by light irradiation, and for example, a photosensitive compound such as furocoumarin derivative may be adopted like the Ia in the general formula (1), and particularly, psoralen derivative is preferable. As specific examples of psoralen derivative, there are psoralen, methoxypsoralen, and trimethylpsoralen.

When the substitution site including the double-stranded nucleic acid binding site Ib is introduced into the general formula (1), plural double-stranded nucleic acid sites exist in the molecule of the intercalator, and consequently, the rate of intercalation into the double-stranded nucleic acid is increased, whereby highly sensitive detection can be carried out.

Both of the double-stranded nucleic acid sites Ia and Ib may comprise any substance so long as it is specifically intercalated into the double-stranded nucleic acid and covalently bonded to the double-stranded nucleic acid by light irradiation. For example, the Ia and the Ib may comprise different substances such that the Ia is methoxypsoralen and the Ib is trimethylpsoralen in the general formula (1).

However, when the Ia and the Ib comprise different substances, the intercalation capability into the double-stranded nucleic acid differs between the Ia and the Ib. Therefore, when quantitative detection is considered, it is desirable that the Ia and the Ib comprise the same substance such that both the Ia and the Ib comprise trimethylpsoralen.

Further, a substance to be used as the electrochemical active site Fb is not restricted so long as it is electrochemically detectable, and a compound having oxidation-reduction property, such as a metal complex having a heterocyclic system compound as a ligand, may be used like the Fa in the general formula (1).

Further, as examples of the metal complex having a heterocyclic system compound as a ligand, there are heterocyclic system compounds including oxygen or nitrogen, for example, metal complexes having a pyridine site or a pyran site as ligands, and particularly, a metal complex having a pyridine site as a ligand is preferable. As examples of the metal complex having a pyridine site as a ligand, there are a metal bipyridine complex and a metal phenanthroline complex.

Further, as examples of a center metal of the metal complex having a heterocyclic system compound as a ligand, there are ruthenium, osnium, zinc, cobalt, platinum, chrome, molybdenum, tungsten, technetium, rhenium, rhodium, iridium, palladium, copper, indium, lanthanum, praseodymium, neodymium, and samarium. Particularly, a complex having ruthenium or osnium as a center metal has favorable electrochemiluminescent characteristic. As examples of the material having favorable electrochemiluminescent characteristic, there are ruthenium bipyridine complex, ruthenium phenanthroline complex, osnium bipyridine complex, and osnium phenanthroline complex.

When the substitution group including the electrochemical active site Fb is introduced into the general formula (1), plural electrochemical active sites exist in the molecule of the intercalator, and consequently, the electrochemical output signal from the intercalator that is bonded to the double-stranded nucleic acid is increased, whereby highly sensitive detection can be carried out.

Both of the electrochemical active sites Fa and Fb may comprise any substance so long as it is electrochemically detectable. For example, the Fa and the Fb may comprise different substances such that the Fa in the general formula (1) is rutheniumbipyridine complex and the Fb in the substitution group is osmiumphenanthroline complex.

However, when the Fa and the Fb comprise different substances, the intensity of the electrochemical detection signal differs between the Fa and the Fb. Therefore, when quantitative detection is considered, it is desirable that the Fa and the Fb comprise the same substance such that both the Fa and the Fb comprise rutheniumbipyridine complex.

Furthermore, a substance to be used as the connecting site Lb or Lc is a substance that connects each of the Fa, the La, and the Ia in the general formula (1) with the Ib or the Fb, and the linker sequence of the connecting site is not particularly restricted, like the La in the general formula 81). For example, alkyl group, —O— group, —CO— group, —NH— group, a-phosphate group, or a group comprising a combination of these groups can be used.

Specific examples of intercalators in which the above-mentioned substitution sites are introduced are shown in (Chemical Formula 1) to (Chemical Formula 10).

[Chemical Formula 1]

[Chemical Formula 2]

[Chemical Formula 3]

[Chemical Formula 4]

-continued

[Chemical Formula 5]

[Chemical Formula 6]

[Chemical Formula 7]

-continued

[Chemical Formula 8]

[Chemical Formula 9]

-continued

[Chemical Formula 10]

The above-mentioned substitution group can be introduced into the intercalator by using a well-known method. For example, in a method utilizing amide binding, an amide bond is formed by reacting the intercalator in which amino group is modified at an end of the site into which the substitution group is to be introduced in the general formula (1), with the substitution group in which carboxyl group is modified at an end of the site to be bonded to the intercalator, whereby the substitution group can be introduced into the intercalator. It is also possible to introduce the substitution group by methods utilizing ester binding, ether binding, thioether binding, carbonyl binding, imino binding and the like.

The above-described intercalator is added before or after hybridization of the gene sample and the nucleic acid probe immobilized onto the electrode.

Then, the double-stranded nucleic acid in which the nucleic acid probe and the gene sample are hybridized is covalently bonded to the intercalator by light irradiation, and thereafter, a washing process for the electrode is carried out.

Thereby, the single-stranded nucleic acid probe that is immobilized onto the electrode surface and does not form double-stranded nucleic acid, and the intercalator that is nonspecifically adsorbed to the electrode surface are removed. As a result, only the intercalator that is specifically covalently bonded to the double-stranded nucleic acid remains in the hybridized double-stranded nucleic acid, and existence of the double-stranded nucleic acid, i.e., the gene sample, can be detected with high sensitivity by measuring an electrochemical signal that is derived from the intercalator.

The electrochemical signal derived from the intercalator can be measured by a measurement system comprising such as a potentiostat and a function generator when an intercalator that generates oxidation-reduction current is used, although it depends on the type of the intercalator to be added. On the other hand, the electrochemical signal can be measured by using a photo multiplier or the like when an intercalator that generates electrochemiluminescence is used.

Example 1

Although examples of the present invention will be described hereinafter, the present invention is not restricted thereto.

(1) Immobilization of Nucleic Acid Probe onto Gold Electrode Surface

A gold electrode is prepared by depositing gold of 200 nm with titan of 10 nm as a base layer, on a glass substrate, using a sputtering apparatus (SH-350 produced by UIVAC, Inc.), and forming an electrode pattern in a photolithography process. The electrode surface is washed for one minute with piranha solution (hydrogen peroxide:concentrated sulfuric acid=1:3), and rinsed with pure water, and then dried by nitrogen blow.

As a nucleic acid probe, there is employed 40-base oligodeoxynucleotide (produced by TAKARA BIO INC.) which is obtained by modifying thiol group via 5'-terminal phosphate group having a sequence of CCCCCTGGAT CCAGATATGC AATAATTTTC CCACTATCAT (SEQ ID NO: 1) that is positioned in the 629-668th from 5'-terminal of a gene sequence of human-derived Cytochrome P-450. Then, the nucleic acid probe is dissolved in 10 mM of PBS (sodium phosphate buffer solution of pH7.4) to adjust it to 100 μM.

Thus adjusted nucleic acid probe solution is dropped onto the gold electrode, and left for four hours at room temperature under saturated humidity, whereby the thiol group and the gold are bonded, thereby to immobilize the nucleic acid probe onto the gold electrode.

(2) Hybridization

As a gene sample, there is employed oligodeoxynucleotide (produced by TAKARA BIO INC.) having a sequence of ATGATAGTGG GAAAATTATT GCATATCTGG ATCCAGGGGG (SEQ ID NO: 2) from the 5'-terminal, which is complementary to the nucleic acid probe. The gene sample is dissolved into a hybridization solution in which 10 mM of PBS and 2×SSC are mixed, and the solution is adjusted to 20 μM.

The adjusted hybridization solution in which the gene sample is dissolved is dropped onto the gold electrode on which the nucleic acid probe is immobilized, and the hybridization solution and the nucleic acid probe are reacted for four hours in a tank that is kept at constant temperature of 40° C., thereby forming double-stranded nucleic acid. Thus, a gold electrode x on which the double-stranded nucleic acid is formed is obtained.

Further, in this example, a gold electrode y on which no double-stranded nucleic acid is formed is prepared as a target for comparison. The gold electrode y having no double-stranded nucleic acid is formed by performing the same processing as that for obtaining the gold electrode x, using a gene sample having a sequence that is non-complementary to the above-mentioned nucleic acid probe (hereinafter referred to as comparison gene sample). In this example, 40 mer Poly-A (produced by TAKARA BIO INC.) having a sequence of AAAAAAAAAA AAAAAAAAAA AAAAAAAAAA AAAAAAAAAA (SEQ ID NO: 3) is used as the comparison gene sample.

(3) Addition of Intercalator

A psoralen-modified ruthenium complex represented by the following chemical formula 11 is used as an intercalator.

[Chemical Formula 11]

Synthesis of the psoralen-modified ruthenium complex is performed according to the following procedure.

In a container filled with nitrogen, 1.0 g (4.4 mmol) of 4,5',8-trimethylpsoralen (produced by Wako Pure Chemical Industries) and 114 mL of high purity (99.6%) acetic acid are added, and psoralen is dissolved in the solution. While heating this solution at 40° C., 7.6 ml (0.10 mol) of chloromethyl methyl ether is dropped. After 24 hours, 7.6 mL of chloromethyl methyl ether is again dropped. After 27 hours and after 40 hours from the dropping, 7.6 mL of chloromethyl methyl ether is added at each time, and reaction is promoted for 4 days. After the reaction, the solution is cooled on ice for 8 hours to separate out a product. This product is collected and washed with cooled diethyl ether to obtain a product A, i.e., 3,4'-dichloromethyl-4,5,8-trimethyl psoralen (yield 25%).

In a container under nitrogen atmosphere, 0.30 g (0.92 mmol) of product A and 0.43 g (2.3 mmol) of phthalimide potassium, which are dissolved in 10 mL of dry dimethylformamide, are added, and the solution is refluxed for 6 hours. The reaction solution is extracted from chloroform, and then washed with 50 mL of 0.2M sodium hydroxide. After the washing, the solvent is distilled away after neutralization, and recrystallization is performed with diethyl ether and chloroform, thereby obtaining a product B (yield 62.4%).

After 0.50 g (0.91 mmol) of product B is dissolved in 30 mL of ethanol, 0.37 mL (7.42 mmol) of hydrazine monohydrate is added, and the solution is reflexed for 3 hours. Thereafter, 20 mL of distilled water and 2.5 mL of hydrochloric acid are added, and the solution is heated and refluxed for more 2 hours. Then, ethanol is distilled away, and the solution is stored in ice for 1 hour, and thereafter, deposited side-reaction product is removed by filtration, and sodium hydrogen carbonate is added to the filtrate to neutralize the same. The reactant is extracted by chloroform, and the solvent is distilled away to obtain a product C (yield 62.1%).

0.15 g (0.52 mmol) of product C dissolved in 5 mL of chloroform and 0.18 mL (1.3 mmol) of triethylamine dissolved in 5 mL of chloroform are added to the container. Thereafter, 1.19 g (10.4 mmol) of glutaric anhydride is added, and the solution is agitated for 9 hours at room temperature. After reaction, the solvent is distilled away, and the crude product is purified by silica gel chromatography to obtain a product D (yield 42%).

After a solution obtained by dissolving 2.50 g ($1.35 \times 10^{-2}$ mol) of 4,4'-dimethyl-2,2'bipyridine in 60.0 mL of THF is injected into a container under nitrogen atmosphere, 16.9 mL ($2.70 \times 10^{-2}$ mol) of lithium diisopropylamide 2M solution is dropped, and the solution is agitated for 30 minutes while cooling the same. On the other hand, 7.61 g ($4.05 \times 10^{-2}$ mol) of 1,2-dibromoethane and 10 mL of THF are added in a container that is similarly dried in nitrogen gas stream, and the solution is agitated while cooling the same. The above-mentioned reaction solution is slowly dropped into this container, and reaction is promoted for 2.5 hours. The reaction solution is neutralized with 2N of hydrochloric acid, and extracted by chloroform after distillation of THF. Further, the crude product obtained by distilling the solvent is purified by silica gel column to obtain a product E (yield 47%).

1.0 g (3.28 mmol) of product E, 0.67 g (3.61 mmol) of phthalimide potassium, and 30.0 mL of dimethylformamide (dehydrated) are added in a container under nitrogen atmosphere, and refluxed for 18 hours in an oil bath. After reaction, the reactant is extracted by chloroform, and washed with 50 mL of 0.2N sodium hydroxide. The solvent is distilled away, and recrystallization is performed by ethyl acetate and hexane, thereby obtaining a product F (yield 61.5%).

After ruthenium chloride (III) (2.98 g, 0.01 mol) and 2,2'-bipyridyl (3.44 g, 0.022 mol) are refluxed for six hours in dimethylformamide (80.0 mL), the solvent is distilled away. Thereafter, acetone is added, and a black precipitation that is obtained by cooling the solution overnight is extracted, and then 170 mL of ethanol aqueous solution (ethanol:water=1:1) is added, and the solution is heated and refluxed for 1 hour. After filtration, 20 g of lithium chloride is added, and ethanol is distilled away, and further, the solution is cooled overnight. The deposited black substance is extracted by suction filtration, thereby obtaining a product G (yield 68.2%).

0.50 g (1.35 mmol) of product F, 0.78 g (1.61 mmol) of product G, and 50 mL of ethanol are added in a container that is nitrogen substituted. After the solution is refluxed for 9 hours under nitrogen atmosphere, the solvent is distilled away, and the resultant is dissolved with distilled water, and precipitated in 1.0M of perchloric acid. This precipitate is collected, and recrystallization is carried out with methanol, thereby obtaining a product H (yield 81.6%).

1.0 g (1.02 mmol) of product H and 70.0 mL of methanol are refluxed for 1 hour. After cooled down to room temperature, 0.21 mL (4.21 mmol) of hydrazine monohydrate is added, and the solution is again refluxed for 13 hours. After reaction, 15 mL of distilled water is added, and methanol is distilled away. Next, 5.0 mL of concentrated hydrochloric acid is added, and a reaction solution obtained after refluxing for 2 hours is cold-stored overnight, and impurities are removed by normal filtration. After this solution is neutralized with sodium hydrogen carbonate, water is distilled away, and inorganic substances are removed with acetonitrile. The crude product obtained by distilling the solvent away is purified with silica gel column, thereby obtaining a product I (yield 71.4%).

0.1 g (0.19 mmol) of product D is dissolved by 10 mL of acetonitrile, and 0.27 g (1.31 mmol) of 1,3-dicyclohexylcarbodiimide is added, and thereafter, the solution is agitated for 3 hours while being cooled, and deposited impurities are removed by filtration. Next, a solution that is obtained by dissolving 0.36 g (0.42 mmol) of product I in 10 mL of acetonitrile and adding 88 µL (0.63 mmol) of triethylamine, which has been agitated at 4° C., is dropped, and the solution is agitated for 24 hours at room temperature. After reaction, a crude product obtained by distilling the solvent away is purified with silica gel column, thereby obtaining the psoralen-modified ruthenium complex represented by (Chemical Formula II) (yield 35.8%). Table 1 shows the result of proton NMR (result of $^1$H-NMR) of the psoralen-modified ruthenium complex obtained as described above.

TABLE 1

| $^1$H-NMR (300 MHz, DMSOd-6) | | |
|---|---|---|
| σ: | 1.39 | (4H, m) |
| | 1.5~1.8 | (8H, m) |
| | 1.9~2.2 | (8H, m) |
| | 2.3~2.6 | (15H, m) |
| | 2.75 | (4H, t) |
| | 3.04 | (4H, t) |
| | 4.29 | (4H, s) |
| | 7.35 | (4H, d) |
| | 7.4~7.6 | (13H, m) |
| | 7.7~7.8 | (8H, m) |
| | 8.15 | (8H, t) |
| | 8.74 | (4H, d) |
| | 8.82 | (8H, d) |

The psoralen-modified ruthenium complex thus obtained is adjusted to 2 µM in 10 mM of PBS.

The adjusted solution is dropped to the gold electrode x on which the double-stranded nucleic acid is formed and to the gold electrode y on which no double-stranded nucleic acid is formed, respectively, and dark reaction is performed for thirty minutes in a refrigerator at 4° C.

(4) Covalent Bonding between Double-Stranded Nucleic Acid and Intercalator

After thirty minutes, the respective gold electrodes x and y are irradiated with ultraviolet ray having a wavelength of 365 nm (5 mW/cm$^2$) for 10 minutes using a UV cross linker (UVPCL-1000L type produced by FUNAKOSHI CO., Ltd.), whereby the psoralen and the double-stranded nucleic acid are covalently bonded. After the covalent bonding, the gold electrode x is vibrated and washed for 10 minutes in 10 mM of PBS to remove unreacted Ru complex.

(5) Electrochemical Measurement

After the above-mentioned processes, an electrolytic solution in which 0.1M of PBS and 0.1M of triethylamine are mixed is dropped to the gold electrode x on which the double-stranded nucleic acid is formed and to the gold electrode y on which no double-stranded nucleic acid is formed, respectively. Thereafter, voltage is applied to the respective gold electrodes x and y, and intercalator-derived electrochemiluminescence which occurs at this time is measured. The voltage application is carried out by scanning from 0V to 1.3V, and the electrochemical measurement is carried out for one second. The measurement of the amount of electrochemiluminescence is carried out using a photoelectron multiplier (H7360-01 produced by Hamamatsu Photonics K.K.), and a maximum amount of luminescence during the voltage scanning is measured.

Figure 1:
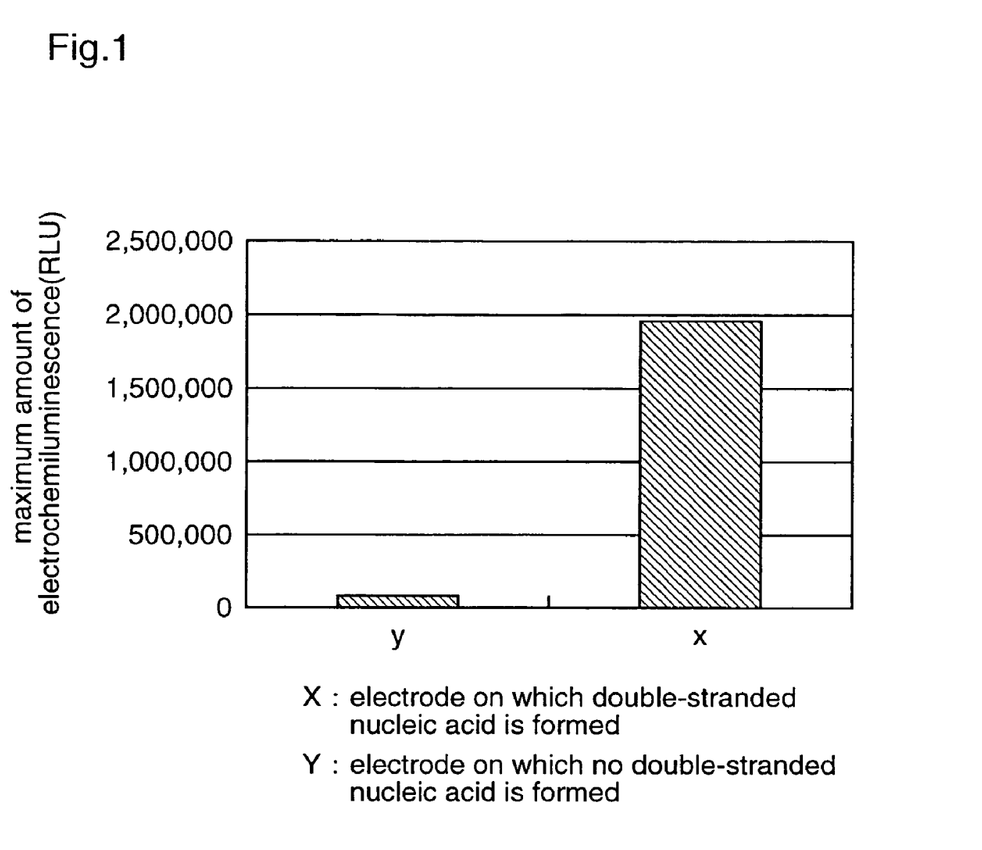
FIG. 1 is a diagram illustrating the maximum amounts of electrochemiluminescence that are detected on an electrode x on which double-stranded nucleic acid is formed and on an electrode y on which no double-stranded nucleic acid is formed, respectively, which are obtained in a first example of the present invention.

FIG. 1 is a diagram illustrating the maximum amounts of electrochemiluminescence that are detected on the electrode x on which the double-stranded nucleic acid is formed and on the electrode y on which no double-stranded nucleic acid is formed. As is evident from FIG. 1, the amount of luminescence on the electrode x on which the double-stranded nucleic acid is formed is significantly larger than the amount of luminescence on the electrode y on which no double-stranded nucleic acid is formed, and it is discovered that detection of the double-stranded nucleic acid can be performed with high sensitivity by using the intercalator according to the this example.

APPLICABILITY IN INDUSTRY

A gene detection method according to the present invention can detects a gene having a specific sequence with high sensitivity, and it is applicable to gene examination, infection examination, genome-based drug discovery, and the like.

The invention claimed is:

1. A gene detection method for detecting a gene having a specific sequence, said method comprising:
   a gene sample conformation step of conforming a gene sample by denaturing a gene to be detected into a single strand;
   an immobilization step of immobilizing, onto an electrode, a single-stranded nucleic acid probe having a base sequence that is complementary to a base sequence of the gene sample to be detected;
   a double-stranded nucleic acid formation step of adding the gene sample to the electrode on which the nucleic acid probe is immobilized, thereby forming a double-stranded nucleic acid in which the nucleic acid probe and the gene sample are hybridized;
   an intercalator addition step of adding, to the electrode on which the double-stranded nucleic acid is formed, an intercalator that has a substitution group comprising one of compounds represented by -Lb-Ib and -Lc-Fb or a combination of the both compounds, at a site shown in a general formula (1):

Fa-La-Ia               (1)

wherein Fa and Fb are electrochemical active sites having electrochemical activity, Ia and Ib are double-stranded nucleic acid binding sites which are specifically intercalated into the double-stranded nucleic acid, and are capable of covalently binding double-stranded nucleic acid by light irradiation, and La, Lb, and Lc are connecting sites which connect the double-stranded nucleic acid binding sites with the electrochemical active sites;
   a light irradiation step of covalently bonding the double-stranded nucleic acid and the intercalator by performing light irradiation; and
   a detection step of detecting the intercalator that is covalently bonded to the double-stranded nucleic acid, by electrochemical measurement
      thereby detecting a gene having a specific sequence in a specimen.

2. A gene detection method as defined in claim 1 wherein the Fa and the Fb comprise the same compound, and the Ia and the Ib comprise the same compound.

3. A gene detection method as defined in claim 1 wherein the detection step applies a voltage to the electrode, and measures an amount of electrochemiluminescence that is caused by the intercalator covalently bonded to the double-stranded nucleic acid.

4. A gene detection method as defined in claim 1 wherein the Ia and the Ib comprise a compound having photosensitivity.

5. A gene detection method as defined in claim 4 wherein the compound having photosensitivity is furocoumarin derivative.

6. A gene detection method as defined in claim 5 wherein the furocoumarin derivative is psoralen derivative.

7. A gene detection method as defined in claim 1 wherein the Fa and the Fb comprise a compound having oxidation-reduction property.

8. A gene detection method as defined in claim 7 wherein the compound having oxidation-reduction property is a compound indicating electrochemiluminescence.

9. A gene detection method as defined in claim 8 wherein the compound indicating electrochemiluminescence is one selected from a group consisting of a metal complex having a heterocyclic system compound as a ligand, rubrene, anthracene, coronene, pyrene, fluoranthene, chrysene, phenanthrene, perylene, binaphthyl, and octatetraene.

10. A gene detection method as defined in claim 9 wherein the metal complex having a heterocyclic system compound as a ligand is a metal complex having a pyridine site as a ligand.

11. A gene detection method as defined in claim 10 wherein the metal complex having a pyridine site as a ligand is one of a metal bipyridine complex and a metal phenanthroline complex.

12. A gene detection method as defined in claim 9 wherein a center metal of the metal complex having a heterocyclic system compound as a ligand is one of ruthenium and osmium.

13. An intercalator which is represented by a general formula (1) as follows:

Fa-La-Ia               (1)

wherein Fa is an electrochemical active site having electrochemical activity, Ia is a double-stranded nucleic acid binding site which is specifically intercalated into the double-stranded nucleic acid and is capable of covalently binding double-stranded nucleic acid by light irradiation, and La is a connecting site which connects the double-stranded nucleic acid binding site with the electrochemical active site; and
   said intercalator having a substitution group at a site shown in formula (1) comprising one of or a combination of both of compounds represented by -Lb-Ib and -Lc-Fb wherein Ib is double-stranded nucleic acid binding site which is specifically intercalated into the double-stranded nucleic acid and is covalently bonded to the double-stranded nucleic acid by light irradiation, Fb is an electrochemical active site having electrochemical activity, and Lb and Lc are connecting sites.

14. An intercalator as defined in claim 13 wherein the Fa and the Fb comprise the same compound, and the Ia and the Ib comprise the same compound.

15. An intercalator as defined in claim 13 wherein the Ia and the Ib comprise a compound having photosensitivity.

16. An intercalator as defined in claim 13 wherein the Fa and the Fb comprise a compound having oxidation-reduction property.

17. An intercalator as defined in claim 16 wherein the compound having oxidation-reduction property is a compound indicating electrochemiluminescence.

18. An intercalator as defined in claim 17 wherein the compound indicating electrochemiluminescence is one selected from a group consisting of a metal complex having a heterocyclic system compound as a ligand, rubrene, anthracene, coronene, pyrene, fluoranthene, chrysene, phenanthrene, perylene, binaphthyl, and octatetraene.

19. An intercalator as defined in claim 18 wherein the metal complex having a heterocyclic system compound as a ligand is a metal complex having a pyridine site as a ligand.

20. An intercalator as defined in claim 19 wherein the metal complex having a pyridine site as a ligand is one of a metal bipyridine complex and a metal phenanthroline complex.

21. An intercalator as defined in claim 18 wherein a center metal of the metal complex having a heterocyclic system compound as a ligand is one of ruthenium and osmium.

22. An intercalator which is represented by a general formula (1) as follows:

Fa-La-Ia               (1)

wherein Fa is an electrochemical active site having electrochemical activity, Ia is a double-stranded nucleic acid binding site which is specifically intercalated into the double-stranded nucleic acid and is capable of covalently binding double-stranded nucleic acid by light irradiation, and La is a connecting site which connects the double-stranded nucleic acid binding site with the electrochemical active site; and said intercalator having a substitution group at a site shown in formula (1) comprising one of or a combination of both of compounds represented by -Lb-Ib and -Lc-Fb wherein Ib is a double-stranded nucleic acid binding site which is specifically intercalated into the double-stranded nucleic acid and is covalently bonded to the double-stranded nucleic acid by light irradiation, Fb is an electrochemical active site having electrochemical activity, and Lb and Lc are connecting sites, and wherein Ia and Ib is a furocoumarin derivative.

23. An intercalator as defined in claim 22 wherein the furocoumarin derivative is psoralen derivative.

* * * * *

```
SEQUENCE LISTING

<160> NUMBER OF SEQ ID NOS: 3

<210> SEQ ID NO 1
<211> LENGTH: 40
<212> TYPE: DNA
<213> ORGANISM: Homo sapiens

<400> SEQUENCE: 1 cccctggat ccagatatgc aataattttc ccactatcat                    40

<210> SEQ ID NO 2
<211> LENGTH: 40
<212> TYPE: DNA
<213> ORGANISM: Homo sapiens

<400> SEQUENCE: 2
atgatagtgg gaaaattatt gcatatctgg atccagggg                    40

<210> SEQ ID NO 3
<211> LENGTH: 40
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: 5'-terminal phosphate group modified by thiol
      group

<400> SEQUENCE: 3
aaaaaaaaaa aaaaaaaaaa aaaaaaaaaa aaaaaaaaaa                   40
```